US006645495B1

(12) United States Patent
Kensil et al.

(10) Patent No.: US 6,645,495 B1
(45) Date of Patent: Nov. 11, 2003

(54) COMPOSITIONS OF SAPONIN ADJUVANTS AND EXCIPIENTS

(75) Inventors: Charlotte A. Kensil, Milford, MA (US); Gerald A. Beltz, Lexington, MA (US)

(73) Assignee: Antigenics, Inc., Woburn, MA (US)

( * ) Notice: Subject to any disclaimer, the term of this patent is extended or adjusted under 35 U.S.C. 154(b) by 0 days.

(21) Appl. No.: 09/143,145

(22) Filed: Aug. 28, 1998

Related U.S. Application Data (60) Provisional application No. 60/057,255, filed on Aug. 29, 1997.

(51) Int. Cl.$^7$ .......................... A61K 39/00; A61K 39/39
(52) U.S. Cl. ............................... 424/184.1; 424/278.1; 424/283.1; 514/44
(58) Field of Search ........................ 424/184.1, 278.1, 424/283.1; 514/44

(56) References Cited

U.S. PATENT DOCUMENTS

| | | | | |
|---|---|---|---|---|
| 4,717,717 A | * | 1/1988 | Finkenaur | 514/21 |
| 5,057,540 A | * | 10/1991 | Kensil et al. | 514/25 |
| 5,595,744 A | * | 1/1997 | Chalmers et al. | 424/253.1 |
| 5,977,081 A | * | 11/1999 | Marciani | 514/25 |
| 6,231,859 B1 | * | 5/2001 | Kensil | 424/184.1 |

FOREIGN PATENT DOCUMENTS

| WO | WO 92/06710 | * | 4/1992 |
|---|---|---|---|
| WO | 93/05789 | * | 4/1993 |
| WO | WO 96/11711 | * | 4/1996 |
| WO | WO96/32401 | * | 10/1996 |

* cited by examiner

*Primary Examiner*—David Saunders
(74) *Attorney, Agent, or Firm*—Pennie & Edmonds, LLP (57) ABSTRACT

Certain novel compositions of the adjuvant saponin QS-21 having improved properties are disclosed. The compositions of the present invention are designed (1) to minimize the lytic effects of QS-21, (2) to improve the tolerance of QS-21 containing formulations in humans or other animals, (3) to stabilize the QS-21 from alkaline hydrolysis and/or (4) to maintain the high adjuvant potency of the QS-21 product. These compositions may be employed with vaccines comprising proteins or peptides, polysaccharides, lipids, or nucleic acids.

15 Claims, 7 Drawing Sheets

COMPOSITIONS OF SAPONIN ADJUVANTS AND EXCIPIENTS

This application claims benefit of United States Provisional Patent Application No. 60/057,255, filed Aug. 29, 1997.

FIELD OF THE INVENTION

The present invention relates to the field of immune adjuvants and the use thereof as immune adjuvants in vaccines. The compositions of the present invention exhibit significantly improved properties relevant to the lytic effect, tolerance to QS-21 associated pain, and product stability of QS-21, and maintain full adjuvant activity.

BACKGROUND OF THE INVENTION

Adjuvant saponins have been identified and purified from an aqueous extract of the bark of the South American tree, *Quillaja saponaria* Molina. Among the 22 peaks which were separable and displayed saponin activity, QS-21 was one of the, more predominant purified saponins. This saponin has been substantially purified by high pressure liquid chromatography (HPLC), low pressure liquid silica chromoatography, and hydrophilic interactive chromatography (HILIC). QS-21 has been found to be useful as an immune adjuvant for enhancing immune responses in individuals at a much lower concentration than the previously available heterogeneous saponin preparations without the toxic effects associated with crude saponin preparations.

QS-21 is a membrane-lytic triterpene glycoside saponin. It forms micelles of approximately the same radius as bovine serum albumin (Kensil, U.S. Pat. No. 5,057,540) and has a critical micellar concentration of approximately 50 μg/ml in PBS (Soltysik, S., et al., 1995, Vaccine 13:1403–1410).

The potency of an adjuvant formulation containing an antigen plus QS-21 can be assessed in experiments that address the relationship of adjuvant dose to immunological function (dose-response experiments). A decrease in adjuvant potency is expected to increase the minimum dose (threshold dose) required for enhancement of immune response. A desirable composition is expected to maintain an equivalent or better potency than the formulation that is used as a reference. For QS-21, the reference formulation is a simple solution in phosphate-buffered saline (PBS) or saline.

The adjuvant activity of QS-21 is assessed in animal models such as mice. The primary responses measured are increases in antigen-specific antibody and antigen-specific cytotoxic T lymphocytes (CTL). The threshold dose of QS-21 that will enhance murine immune response (antibody or CTL) has been measured in simple buffer solution such as PBS. A dose of 2.5 μg has been shown to be the threshold dose for antibody (Kensil, C. R., et al., 1993, *Vaccine Research* 2:273–281) and for CTL (Newman, M. J., et al., 1992, *J. Immunology* 148:2357–2362) to the antigen ovalbumin (OVA) in C57BL/6 mice in PBS. Similar threshold doses were observed when aluminum hydroxide was included in the PBS formulation (Kensil, C. R., et al., 1993, *Vaccine. Research* 2:273–281). However, it is expected that there may be differences in potency between different compositions of a given adjuvant.

Despite these beneficial qualities, QS-21 possesses some unwelcome qualities as well. For instance, QS-21 associates with phospholipid bilayers and causes a lytic effect on certain cell membranes (i.e., erythrocytes). QS-21 will absorb to the phospholipid bilayer of sheep erythrocytes and cause the red blood cells to release hemoglobin. This hemoglobin release, which is known as hemolysis, occurs at a concentration of approximately 5–7 μg/ml in a simple buffer such as saline or PBS (Kensil, C. R., et al., 1991, *J. Immunology* 146:431–437). At higher concentrations (above the critical micellar concentration of QS-21), total lysis of the red blood cell membrane occurs is, therefore, an undesirable property for a composition.

In in vivo studies, hemolysis is not noted. However, after intramuscular injection of QS-21/saline solutions into New Zealand white rabbits, mild to moderate fibroblast damage or necrosis is noted in some animals when the injection site is analyzed histopathologically (Kensil, C. R., et al., 1995, In: *Vaccine Design: The Subunit and Adjuvant Approach*, Powell, M. F. and Newman, M. J., Eds., Plenum Press, NY). Further, creatine kinase, a marker for muscle damage is increased after injection with QS-21 in saline or PBS. This rise is believed to be due to the lytic effect of QS-21 on cell membranes.

Moreover, in clinical trials, some individuals have experienced an immediate, transient pain after injection with QS-21 in simple buffer solutions (saline or PBS). This pain, described by most individuals as a burning pain, may be a secondary reaction correlated with the lytic effect of the QS-21 adjuvant. Patient pain is likewise an objectionable property for a composition.

Product stability is another concern for QS-21 containing compositions. The shelf life of a vaccine product is typically defined by the extent of time to reach a defined and acceptable low level of degradation (such as, the time to 10% degradation, also known as $t_{90}$). Most commercial vaccine products have a shelf life of at least 18 to 24 months when stored in the refrigerator at 4° C. Adjuvants, which are essential components of vaccines, therefore must also have equally long shelf lives. However, the shelf life of a 50 μg/ml solution of QS-21 at pH 7.0 at 4° C. is reached in about 3 months. The reason for the short shelf life is because the ester bond of QS-21 is increasingly labile at increasing pH and because monomers of QS-21, as opposed to micelles, are subject to hydrolysis. The need to stabilize compositions of QS-21 adjuvant is significant.

SUMMARY OF THE INVENTION

A need exists for compositions of the saponin adjuvant QS-21 that may be used to boost the antigenic immune response in a relatively low dose with low local reactions and side effects, but also features a reduced lytic effect, improved tolerance to QS-21, and an increased stability. Accordingly, the present invention provides novel compositions of QS-21 that have these improved characteristics compared to a simple solution of QS-21 in a buffer such as saline or PBS. Surprisingly, the full adjuvant potency of QS-21 in the disclosed compositions is not compromised compared to a control formulation of QS-21 in PBS.

DESCRIPTION OF THE FIGURES

FIG. 1 depicts a graph showing the adjuvant potency of various compositions.

DESCRIPTION OF THE PREFERRED EMBODIMENTS

The saponins of the present invention may be obtained from the tree *Quillaja saponaria* Molina.

The term "saponin" as used herein includes glycosidic triterpenoid compounds which produce foam in aqueous solution, have hemolytic activity in most cases, and possess immune adjuvant activity. The invention encompasses the saponin per se, as well as biologically active fragments thereof.

The invention also concerns compositions, such as immunologic compositions, comprising one or more substantially pure saponin fractions, and methods of using these compositions as immune adjuvants.

More particularly, the compositions of the present invention may reduce the in vitro lytic effects of a saponin adjuvant containing formulation. Another preferred composition is one that may maintain the maximum adjuvant activity of a saponin. Yet another preferred composition may increase the stability of a saponin adjuvant containing composition from alkaline hydrolysis. Other compositions may preferably improve an individual's tolerance to saponin adjuvant associated pain from a formulation containing a saponin adjuvant.

As described in Kensil, et al., U.S. Pat. No. 5,057,540, the contents of which are fully incorporated by reference herein, the adjuvant activity of such saponins may be determined by any of a number of methods known to those of ordinary skill in the art. The increase in antibody titer of antibody against specific antigen upon administration of an adjuvant may be used as a criteria for adjuvant activity. (Dalsgaard; *Acta Verterinia Scandinavica*, 69:1 (1978); Bomford, *Int. Archs. Allergy Appl. Immun.* 77:409 (1985).) Briefly, one such test involves injecting CD-1 mice intradermally with an antigen (for instance, i.e., bovine serum albumin, BSA) mixed with varying amounts of the potential adjuvant. Sera was harvested from the mice two weeks later and tested by ELISA for anti-BSA antibody.

"QS-21" designates the mixture of isomeric components QS-21-V1 and QS-21-V2 which appear as a single peak on reverse phase HPLC on Vydac C4 (5 μm particle size, 300 Å pore, 4.6 mm ID×25 cml) in 40 mM acetic acid in methanol/water (58/42, v/v). The component fractions are referred to specifically as QS-21-V1 and QS-21-V2 when describing experiments performed on the further purified components.

The term "substantially pure" means substantially free from compounds normally associated with the saponin in its natural state and exhibiting constant and reproducible chromatographic response, elution profiles, and biologic activity. The term "substantially pure" is not meant to exclude artificial or synthetic mixtures of the saponin with other compounds.

The substantially pure QS-7 saponin also referred to as QA-7 in U.S. Pat. No. 5,057,540) is characterized as having immune adjuvant activity, containing about 35% carbohydrate (as assayed by anthrone) per dry weight, having a UV absorption maxima of 205–210 nm, a retention time of approximately 9–10 minutes on RP-HPLC on a Vydac $C_4$ column having a 5 μm particle size, 300 Å pore, 4.6 mm ID×25 cm L in a solvent of 40 mM acetic acid in methanol/water (58/42; v/v) at a flow rate of 1 ml/min, eluting with 52–53% methanol form a Vydac $C_4$ column having a 5 μm particle size, 300 Å pore, 10 mM ID×25 cm L in a solvent of 40 mM acetic acid with gradient elution from 50 to 80% methanol, having a critical micellar concentration of approximately 0.06% (w/v) in water and 0.07% (w/v) in phosphate buffered saline, causing no detectable hemolysis of sheep red blood cells at concentrations of 200 μg/ml or less, and containing the monosaccharide residues terminal rhamnose, terminal xylose, terminal glucose, terminal galactose, 3-xylose, 3,4-rhamnose, 2,3-fucose, and 2,3-glucuronic acid, and apiose (linkage not determined).

The substantially pure QS-17 saponin (also referred to as QA-17 in U.S. Pat. No. 5,057,540) is characterized as having immune adjuvant activity, containing about 29% carbohydrate (as assayed by anthrone) per dry weight, having a UV absorption maxima of 205–210 nm, a retention time of approximately 35 minutes on RP-HPLC on a Vydac $C_4$ column having a 5 μm particle size, 300 Å pore, 4.6 mm ID×25 cm L in a solvent of 40 mM acetic acid in methanol/water (58/42; v/v) at a flow rate of 1 ml/min, eluting with 63–64% methanol from a Vydac $C_4$ column having a 5 μm particle size, 300 Å pore, 10 mM ID×25 cm L in a solvent of 40 mM acetic acid with gradient elution from 50 to 80% methanol, having a critical micellar concentration of approximately, 0.06% (w/v) in water and 0.03% (w/v) in phosphate buffered saline, causing hemolysis of sheep red blood cells at 25 μg/ml or greater, and containing the monosaccharide residues terminal rhamnose, terminal xylose, 2-fucose, is characterized as having immune adjuvant activity, containing about 35% carbohydrate (as assayed by anthrone) per dry weight, having a UV absorption maxima of 205–210 nm, a retention time of approximately 9–10 minutes on RP-HPLC on a Vydac $C_4$ column having a 5 μm particle size, 300 Å pore, 4.6 mm ID×25 cm L in a solvent of 40 mM acetic acid in methanol/water (58/42; v/v) at a flow rate of 1 ml/min, eluting with 52–53% methanol form a Vydac $C_4$ column having a 5 μm particle size, 300 Å pore, 10 mM ID×25 cm L in a solvent of 40 mM acetic acid with gradient elution from 50 to 80% methanol, having a critical micellar concentration of approximately 0.06% in water and 0.07% in phosphate buffered saline, causing no detectable hemolysis of sheep red blood cells at concentrations of 200 μg/ml or less, and containing the monosaccharide residues terminal rhamnose, terminal xylose, 2-fucose, 3-xylose, 3,4-rhamnose, 2,3-glucuronic acid, terminal glucose, 2-arabinose, terminal galactose and apiose (linkage not determined).

The substantially pure QS-18 saponin (also referred to as QA-18 in U.S. Pat. No. 5,057,540) is characterized as having immune adjuvant activity, containing about 25–26% carbohydrate (as assayed by anthrone) per dry weight, having a UV absorption maxima of 205–210 nm, a retention time of approximately 38 minutes on RP-HPLC on a Vydac $C_4$ column having a 5 µm particle size, 300 Å pore, 4.6 mm ID×25 cm L in a solvent of 40 mM acetic acid in methanol/water (58/42; v/v) at a flow rate of 1 ml/min, eluting with 64–65% methanol from a Vydac $C_4$ column having a 5 µm particle size, 300 Å pore, 10 mM ID×25 cm L in a solvent of 40 mM acetic acid with gradient elution from 50 to 80% methanol, having a critical micellar concentration of approximately 0.04% (w/v) in water and 0.02% (w/v) in phosphate buffered saline, causing hemolysis of sheep red blood cells at 25 µg/ml or greater, and containing the monosaccharide residues terminal arabinose, terminal apiose, terminal xylose, terminal glucose, terminal galactose, 2-fucose, 3-xylose, 3,4-rhamnose, and 2,3-glucuronic acid.

The substantially pure QS-21 saponin (also referred to as QA-21 in U.S. Pat. No. 5,057,540) is characterized as having immune adjuvant activity, containing about 22% carbohydrate (as assayed by anthrone) per dry weight, having a UV absorption maxima of 205–210 nm, a retention time of approximately 51 minutes on RP-HPLC on a Vydac $C_4$ column having a 5 µm particle size, 300 Å pore, 4.6 mm ID×25 cm L in a solvent of 40 mM acetic acid in methanol/water (58/42; v/v) at a flow rate of 1 ml/min, eluting with 69–70% methanol from a Vydac $C_4$ column having a 5 µm particle size, 300 Å pore, 10 mM ID×25 cm L in a solvent of 40 mM acetic acid with gradient elution from 50 to 80% methanol, having a critical micellar concentration of approximately 0.03% (w/v) in water and 0.02% (w/v) in phosphate buffered saline, causing hemolysis of sheep red blood cells at 25 µg/ml or greater. The component fractions, substantially pure QS-21-V1 and QS-21-V2 saponins, have the same molecular weight and identical spectrums by FAB-MS. They differ only in that QS-21-V1 has a terminal apiose which is xylose in QS-21-V2 (which therefore has two terminal xyloses and no apiose). The two components additionally contain the monosaccharides terminal arabinose, terminal apiose, terminal xylose, 4-rhamnose, terminal galactose, 2-fucose, 3-xylose, and 2,3-glucuronic acid.

The invention may also encompass impure forms of saponin adjuvants. For example, one preferred embodiment is the heterogenic saponin adjuvant known as "Quil A." Commercial preparations of Quil A are available from Superfos (Vedbaek, Denmark) and have been isolated from the bark of the South American tree, *Quillaja saponaria* Molina. Quil A is characterized chemically as carbohydrate moieties in glycosidic linkage to the triterpenoid quillaic acid. Quil A possesses immune adjuvant activity and separates into 20 discrete peaks by RP-HPLC on Vydac $C_4$ column having a 5 µm particle size, 300 Å pore, 4.6 mM ID×25 cm L in a solvent of 40 mM acetic acid in methanol water (U.S. Pat. No. 5,057,540).

The invention also relates to a composition which comprises a saponin adjuvant of the present invention, an antigen, and an excipient. Preferably, the adjuvant is QS-21. Preferably, the excipients may be nonionic surfactants, polyvinylpyrollidone, human serum albumin, aluminum hydroxide, agents with anesthetic action, and various unmodified and devivatized cyclodextrins. More preferably, the nonionic surfactants may include Polysorbate 20, Polysorbate 40, Polysorbate 60, and Polysorbate 80. The polyvinylpyrollidone may preferably be Plasdone C15, a pharmaceutical grade of polyvinylpyrollidone. The agent having anesthetic action preferably is benzyl alcohol. A preferred cyclodextrin is a hydroxypropyl-β-cyclodextrin, which reduces QS-21 lysis of red blood cells in vitro.

The term "immune adjuvant," as used herein, refers to compounds which, when administered to an individual or tested in vitro, increase the immune response to an antigen in the individual or test system to which said antigen is administered. Preferably, such individuals are humans, however, the invention is not intended to be so limiting. Any animal that may experience the beneficial effects of the vaccines of the invention are within the scope of animals which may be treated according to the claimed invention. Some antigens are weakly immunogenic when administered alone or are toxic to the individual at concentrations which evoke immune responses in said individual. An immune adjuvant may enhance the immune response of the individual to the antigen by making the antigen more strongly immunogenic. The adjuvant effect may also lower the dose of said antigen necessary to achieve an immune response in said individual.

The saponins of the present invention may be utilized to enhance the immune response to any antigen. Typical antigens suitable for the immune-response provoking compositions of the present invention include antigens derived from any of the following: viruses, such as influenza, feline leukemia virus, feline immunodeficiency virus, HIV-1, HIV-2, rabies, measles, hepatitis B, or hoof and mouth disease, bacteria, such as anthrax, diphtheria, Lyme disease or tuberculosis; or protozoans, such as Babeosis bovis or Plasmodium. The antigens may be proteins, peptides, polysaccharides, lipids, or nucleic acids encoding the protein or peptide. The proteins, peptides, lipids, or nucleic acids may be purified from a natural source, synthesized by means of solid phase synthesis, or may be obtained means of recombinant genetics.

Administration of the compounds useful in the method of the present invention may be by parenteral, intravenous, intramuscular, subcutaneous, intranasal, oral or any other suitable means. The dosage administered may be dependent upon the age, weight, species, kind of concurrent treatment, if any, route of administration, and nature of the antigen administered. In general, the saponin and antigen may be administered at a dosage of about 0.001 to about 1.0 mg/kg of saponin adjuvant or antigen per weight of the individual. The initial dose may be followed up with a booster dosage after a period of about four weeks to enhance the immunogenic response. Further booster dosages may also be administered.

The effective compound useful in the method of the present invention may be employed in such forms as capsules, liquid solutions, suspensions or elixirs for oral administration, or sterile liquid forms such as solutions or suspensions. The vaccine of the present invention may be administered parenterally, intranasally, or orally.

Another preferred embodiment is a method for reducing the in vitro lytic effect of an immune adjuvant composition comprising administering to an individual an effective amount of QS-21 and an excipient. Preferably, the excipients may be nonionic surfactants, polyvinylpyrollidone, human serum albumin, aluminum hydroxide, agents with anesthetic action, and various unmodified and devivatized cyclodextrins. More preferably, the nonionic surfactants may include Polysorbate 20, Polysorbate 40, Polysorbate 60, and Polysorbate 80. The polyvinylpyrollidone may preferably be Plasdone C15, a pharmaceutical grade of polyvinylpyrrolidone. The agent having anesthetic action preferably is benzyl alcohol. A preferred cyclodextrin is Encapsin, a hydroxypropyl-β-cyclodextrin, which reduces QS-21 lysis of red blood cells in vitro.

Other preferred methods falling within the scope of the invention include a method for maintaining the maximum adjuvant activity of QS-21 comprising administering to an individual an effective amount of QS-21 and an excipient and a method for improving the tolerance to saponin adjuvant associated pain in an individual to whom it is administered comprising administering an effective amount of QS-21 and an excipient.

EXAMPLES

A variety of excipients were evaluated in combination with QS-21 as novel compositions. These included various nonionic surfactants (Triton X-100, Polysorbate 20, Polysorbate 40, Polysorbate 60, and Polysorbate 80), polyvinylpyrollidone (Plasdone C15), human serum albumin, aluminum hydroxide, agents with anesthetic action (benzyl alcohol), and various unmodified and derivatized cyclodextrins (hydroxypropyl-β-cyclodextrin, hydroxypropyl-γ-cyclodextrin, methyl-β-cyclodextrin). The final formulations were assessed for their capacity to reduce the lytic effect of QS-21, to improve tolerance to QS-21 adjuvant associated pain in humans, to stabilize QS-21 in aqueous solution, and/or to maintain maximum adjuvant potency relative to a control formulation of QS-21 in PBS.

Example 1

Compositions that Reduce the Lytic Effect of QS-21

A simple in vitro assay was used to screen excipients for reducing the lytic effect of QS-21. The lytic effect of QS-21 can be determined in an assay of hemolysis of sheep erythrocytes. Briefly, various two fold serial dilutions of QS-21 in a given excipient are prepared in a round bottom microtiter plate (100 μl/well). All plates contain control wells containing excipient, but no QS-21. The concentration of QS-21 ranges from 1.56 to 200 μg/ml. A total volume of 25 μl of sheep erythrocytes (washed with PBS) is added to each well, mixed with the QS-21/excipient solution, and incubated at ambient temperature for 30 minutes. After the end of the incubation, the round bottom plate is centrifuged at 2000 rpm for 5 minutes to sediment any unlysed cells. A total volume of 75 μl of supernatant (containing released hemoglobin) is transferred to the equivalent well of a flat-bottom 96 well plate. The flat-bottom plate is centrifuged at 2000 rpm for 5 minutes to break any air bubbles. The absorbance at 570 nm is read in a microtiter plate reader. Absorbance at 570 nm is plotted on the y-axis against QS-21 concentration plotted on the x-axis. The absorbance of hemoglobin in the supernatant of a well where no intact cell pellet was observed is defined as maximum hemolysis. The hemolytic index of QS-21 is defined as the concentration of QS-21 that yields an absorbance equivalent to 50% of the maximum absorbance. An excipient that reduces the lytic effect of QS-21 is expected to increase the hemolytic index.

Table 1 lists the hemolytic indices of QS-21 in various excipients. All excipients were tested in the absence of QS-21. In the absence of QS-21, no hemolysis was noted, indicating that the excipient formulations were isotonic. Excipients that were shown to be effective in minimizing the lytic effect (increase hemolytic index) of QS-21 were hydroxypropyl-β-cyclodextrin, aluminum hydroxide, and Polysorbate 80 in saline.

TABLE 1

| Excipient | Hemolytic Index (μg/ml) |
|---|---|
| PBS | 5 |
| α-cyclodextrin (2 mg/ml) | 1.5 |
| β-cyclodextrin (2 mg/ml) | 10 |
| methyl-β-cyclodextrin (2 mg/ml) | 36 |
| hydroxypropyl-γ-cyclodextrin (2 mg/ml) | 5 |
| hydroxypropyl-β-cyclodextrin (1 mg/ml) | 9 |
| hydroxypropyl-β-cyclodextrin (2 mg/ml) | 11 |
| hydroxypropyl-β-cyclodextrin (4 mg/ml) | 18 |
| hydroxypropyl-β-cyclodextrin (8 mg/ml) | 32 |
| hydroxypropyl-β-cyclodextrin (16 mg/ml) | 51 |
| hydroxypropyl-β-cyclodextrin (32 mg/ml) | 93 |
| human serum albumin (40 mg/ml) | 9 |
| QS-7 (250 μg/ml) | 30 |
| aluminum hydroxide (2 mg/ml) in PBS | 5 |
| aluminum hydroxide (2 mg/ml) in saline | 13 |
| Monophosphoryl lipid A (25 μg/ml) | 4.9 |
| Monophosphoryl lipid A (50 μg/ml) | 7.7 |
| Monophosphoryl lipid A (100 μg/ml) | 6.5 |
| Triton X-100 (50 μg/ml) | 1 |
| Triton X-100 (100 μg/ml) | 1 |
| Polysorbate 80 (2 mg/ml) | 9 |
| Polysorbate 80 (4 mg/ml) | 18 |
| Polysorbate 80 (10 mg/ml) | 38 |

Example 2

Compositions that Reduce the Lytic Effects of Other Saponins

Other saponin adjuvants are also known to be hemolytic, although to different extent than QS-21. These saponins include substantially pure QS-7, QS-17, and QS-18. In addition, heterogeneous adjuvant saponins such as Quil A are hemolytic. An example of the effect of Polysorbate 80 and hydroxypropyl-β-cyclodextrin on the hemolytic indices of the substantially pure QS-7 and heterogeneous Quil A is shown in Table 2. Hydroxypropyl-β-cyclodextrin was shown to be effective in reducing the lytic effect (increasing the hemolytic index) of QS-7. Polysorbate 80 and hydroxypropyl-β-cyclodextrin were shown to be effective in minimizing the lytic effect (increasing the hemolytic index) of Quil A.

TABLE 2

| Saponin | Excipient | Hemolytic Index (μg/ml) |
|---|---|---|
| QS-7 | PBS | 650 |
| QS-7 | Polysorbate 80 (8 mg/ml) | 60 |
| QS-7 | Hydroxypropyl-β-cyclodextrin (32 mg/ml) | >1000 |
| Quil A | PBS | 18 |
| Quil A | Polysorbate 80 (8 mg/ml) | 43 |
| Quil A | Hydroxypropyl-β-cyclodextrin (32 mg/ml) | 200 |

Example 3

Compositions that Stabilize QS-21

QS-21 is an acylated bidesmodic triterpene saponin. It has a fatty acid ester linked to the hydroxyl residues of fucose. In aqueous solution, this fatty acid ester migrates between two adjacent vicinal hydroxyl groups (fucose 3, 4) to form two equilibrium isomers Jacobsen, N. E., Fairbrother, W. J., et al., 1996, Carbohydrate Research 280:1–14). The predominant isomer is acylated at fucose 4 and the minor isomer is acylated at fucose 3. This ester bond is the most labile bond in QS-21 and will hydrolize under alkaline conditions to form a deacylated saponin and a fatty acid-arabinose domain. The deacylated saponin and the fatty acid domain are both inactive as immunological adjuvants (Kensil, C. R., et al., 1996, In: Saponins Used in Traditional and Modern Medicine, Waller and Yamaski, Eds., Plenum Press, NY, 165–172). Various conditions affect the stability of this ester bond (Cleland, J. L., et al., 1996, J. Pharmaceutical Sciences 85:22–28). Furthermore, the monomer form of QS-21 is more susceptible to hydrolysis than the micellar form.

Examples of the shelf life of QS-21 are shown in Table 3. The aqueous shelf life for a 50 μg/ml QS-21 solution at pH 7.0 at 4° C. was shown to be only 94 days or approximately 3 months. This is representative of a typical clinical vaccine formulation containing QS-21 adjuvant (which consists of QS-21 at a concentration of 50–200 μg/ml in a-physiological pH buffer (pH 7.0–7.5)). Hence, in simple buffer and salt solutions at low concentration, the QS-21 product does not maintain a desirable stability profile. Some improvement in stability, however, can be achieved by an increased concentration of the QS-21 product. For instance, the shelf life of a 500 μg/ml QS-21 solution at pH 7.0 at 4° C. was shown to be 717 days, or 23.9 months. But a concentrated QS-21 solution is not necessarily a practical method of administering a low dose of adjuvant. For example, administration of 25 μg from a 500 μg/ml solution would require the syringe withdrawal of 0.05 ml of dose. Additionally, some improved stability can be achieved by the use of a lower pH, i.e., at pH 6.0. However, a pH substantially lower than the physiological pH range may not be tolerated well or be compatible with the antigen.

TABLE 3

| QS-21 Concentration | pH | $t_{90}$ (days) |
| --- | --- | --- |
| 50 μg/ml | pH 7.0 | 94 |
| 50 μg/ml | pH 6.0 | 679 |
| 500 μg/ml | pH 7.0 | 717 |

Another way to evaluate the stability of QS-21 in aqueous solution was to assay the solution by HPLC in an accelerated stability assay at 37° C. Although this is not the temperature used for storage of vaccines (4° C.), it was expected that this assay at 37° C. would show the relative stabilizing power of a given excipient. For example, an excipient that extended the $t_{90}$ value by two fold at 37° C. would also be expected to extend the $t_{90}$ value by two fold at 4° C.

Specifically, QS-21 (100 μg/ml) was prepared in various excipients in PBS at pH 7.0. The solutions were incubated at 37° C. for 7 days. At the end of 7 days, the solutions were assayed by reversed phase-HPLC to determine the extent of degradation. The data was plotted as log (fraction QS-21 t=7/QS-21 t=0 days) against time on the x-axis. The time to 10% degradation ($t_{90}$) was extrapolated from this plot.

Table 4 shows the $t_{90}$ values of QS-21 in various excipients. Stabilization of QS-21 is shown by an increase in $t_{90}$. Excipients that stabilized QS-21 by at least two fold are Polysorbate 20, Polysorbate 80, native Quillaja saponin QS-7, and the deacylsaponin resulting from alkaline hydrolysis of QS-21 (DS-1).

TABLE 4

| Excipient | $t_{90}$ (days) at 37° C. |
| --- | --- |
| PBS (pH 7.0) | 1.2 |
| Polysorbate 20 (720 μg/ml) | 2.9 |
| Polysorbate 80 (250 μg/ml) | 3.2 |
| Polysorbate 80 (500 μg/ml) | 4.3 |
| Polysorbate 80 (1.0 mg/ml) | 5.2 |
| Polysorbate 80 (2.0 mg/ml) | 7.2 |
| Phenol (2.5 mg/ml) | 2.3 |
| Pluronic F68 (1.0 mg/ml) | 1.4 |
| QS-7 (100 μg/ml) | 1.8 |
| QS-7 (250 μg/ml) | 2.6 |
| QS-7 (500 μg/ml) | 9.0 |
| QS-7 (1.0 mg/ml) | 16.0 |
| DS-1 (100 μg/ml) | 2.2 |
| DS-1 (250 μg/ml) | 3.3 |
| DS-1 (500 μg/ml) | 7.2 |
| DS-1 (1.0 mg/ml) | 6.2 |
| Monocaproyl-rac-glycerol (1.0 mg/ml) | 1.7 |
| α-cyclodextrin (5 mg/ml) | 0.8 |
| β-cyclodextrin (5 mg/ml) | 0.7 |
| Methyl-β-cyclodextrin (5 mg/ml) | 1.5 |
| hydroxypropyl-γ-cyclodextrin (5 mg/ml) | 1.0 |
| hydroxypropyl-β-cyclodextrin (5 mg/ml) | 1.0 |

In addition, 0.9% benzyl alcohol, and Plasdone C15 were evaluated for its ability to stabilize QS-21 (Table 5). All QS-21 concentrations and incubation conditions were equivalent in this experiment except that the QS-21 formulation was prepared in Dulbecco's PBS (without calcium or magnesium) at pH 7.5. As expected, the higher pH resulted in a faster degradation of QS-21 in PBS. However, Plasdone C15 stabilized QS-21.

TABLE 5

| Excipient | $t_{90}$ (days) at 37° C., pH 7.5 |
| --- | --- |
| Dulbecco's PBS | 0.6 |
| 0.9% benzyl alcohol in Dulbecco's PBS | 0.7 |
| Plasdone C15 in Dulbecco's PBS (25 mg/ml) | 1.6 |
| Plasdone C15 in Dulbecco's PBS (50 mg/ml) | 7.7 |

Example 4

Adjuvant Potency of Compositions

Figure 1A:
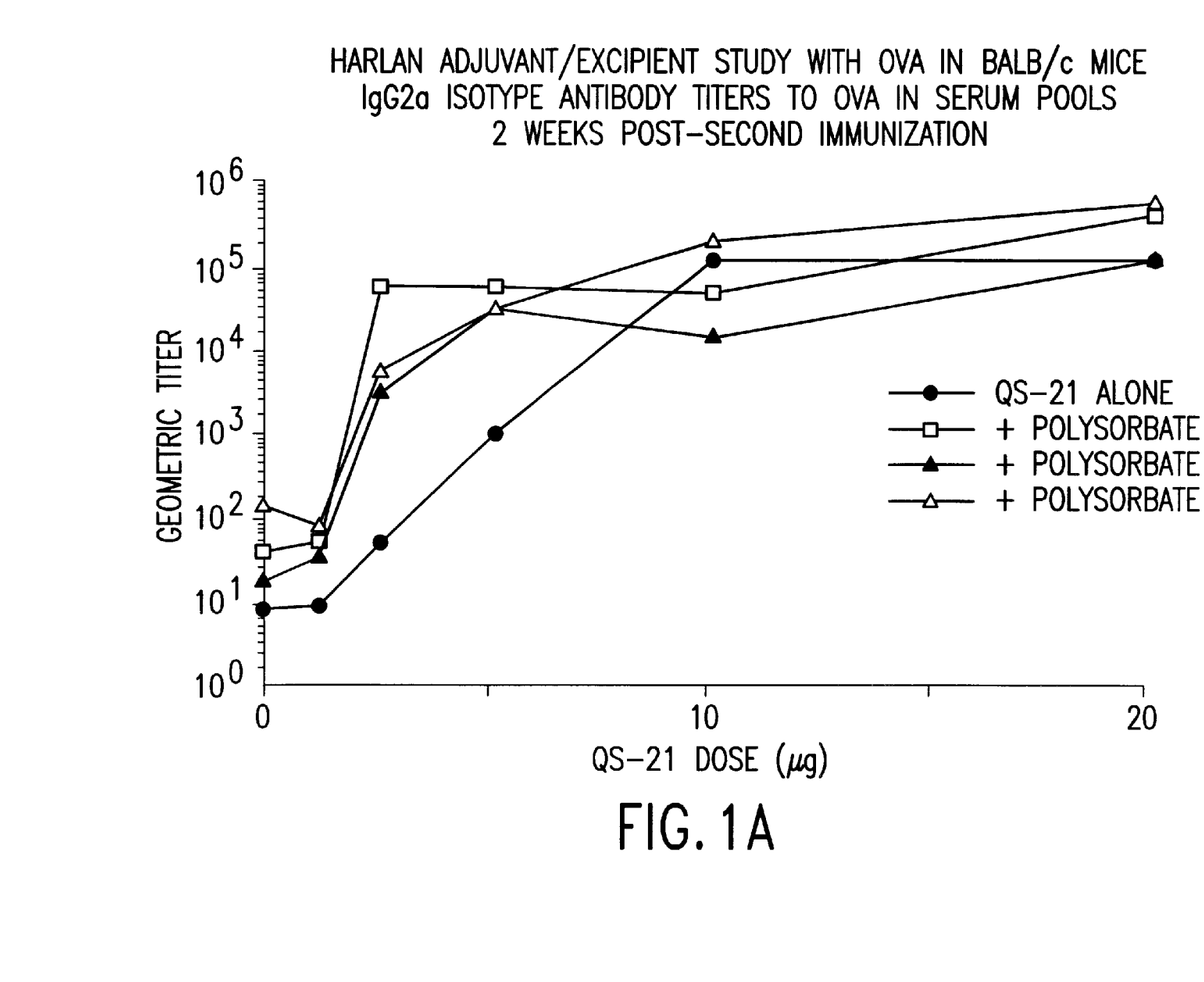
FIG. 1A shows the effect of Polysorbate 40, Polysorbate 60, and Polysorbate 80 on the immune response of Balb/c mice to ovalbumin at different concentrations of QS-21.
Figure 1B:
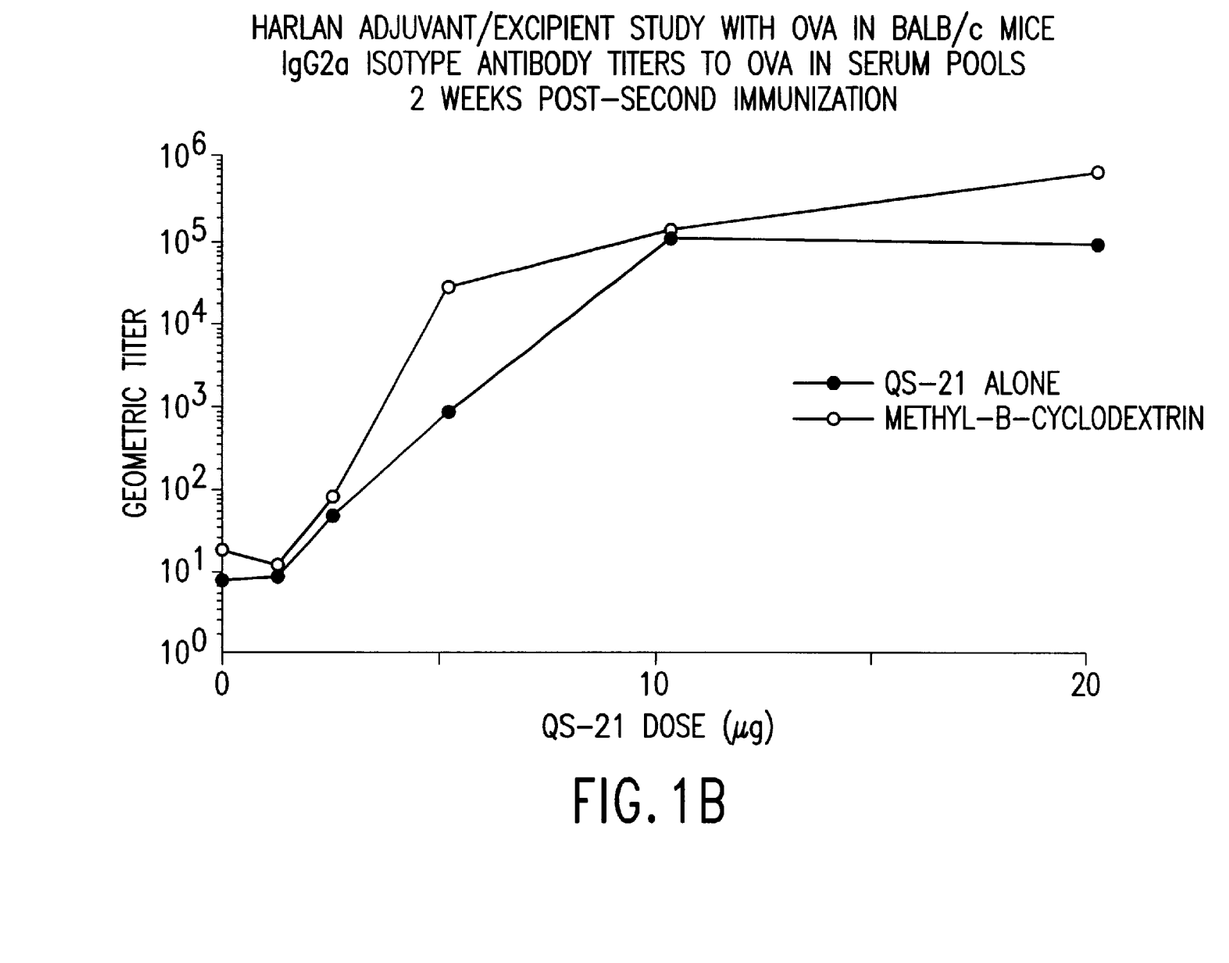
FIG. 1B shows the effect of methyl-β-cyclodextrin on the immune response of Balb/c mice to ovalbumin at different concentrations of QS-21.

FIGS. 1A and 1B show the effect of Polysorbate 40, Polysorbate 60, Polysorbate 80, and methyl-β-cyclodextrin on the immune response of Balb/c mice to OVA plus various doses of QS-21. Female mice (10/group, 8–10 weeks of age at the first immunization) were immunized subcutaneously with 5 μg of OVA and the indicated dose of QS-21 in either PBS alone or in 2 mg/ml excipient in PBS. A booster immunization was given by the same route at week 2. Sera was collected at week 4 for EIA analysis of the anti-OVA response. Mice were analyzed for OVA-specific IgG2a by a standard EIA analysis. (Kensil, C. R., et al., 1993, Vaccine Research 2:273–281) QS-21 was active in all excipients within two fold of the threshold value determined in PBS. The same maximum level of antibody response was reached at the optimum adjuvant dose (typically 10 μg and above).

Figure 2:
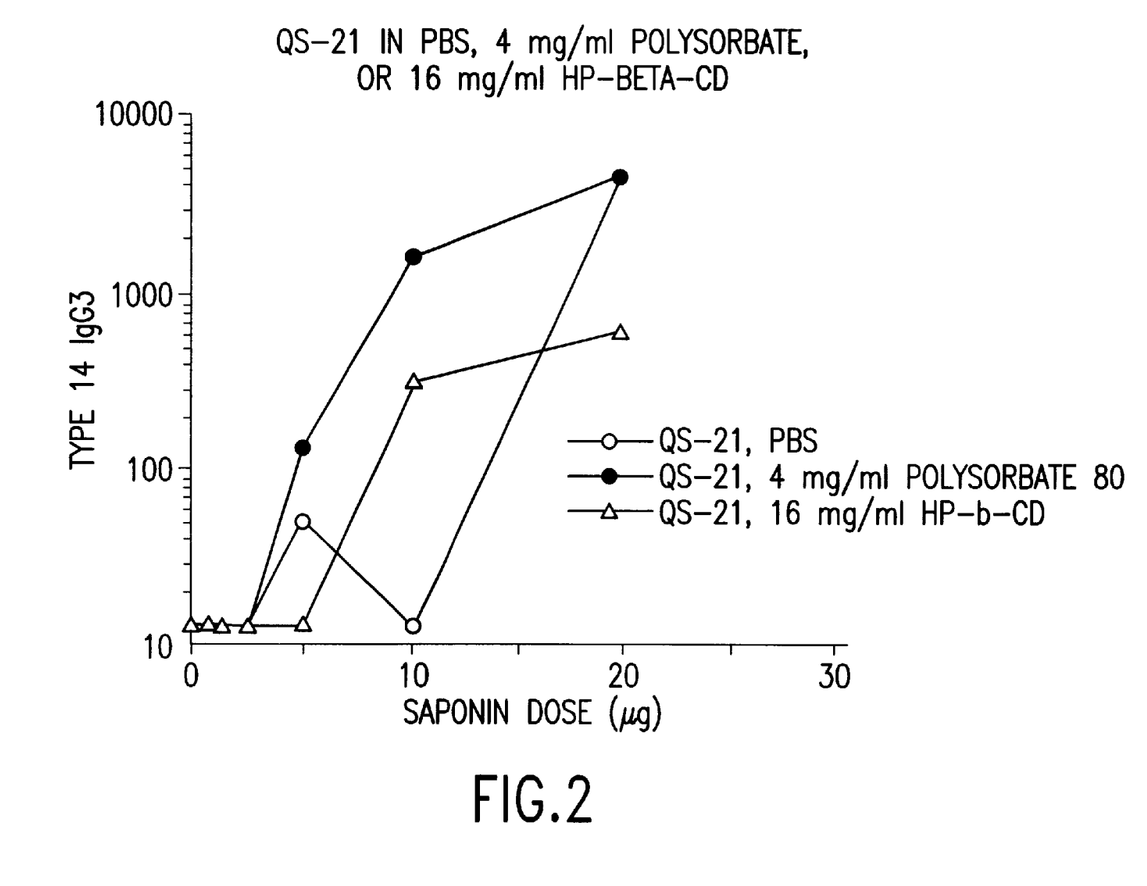
FIG. 2 depicts a graph showing the effect of Polysorbate 80 and hydroxypropyl-β-cyclodextrin on Type 14 IgG3 antibody response to a T-independent polysaccharide antigen.

FIG. 2 shows the effect of excipients on antibody response to a T-independent polysaccharide antigen. Balb/c mice were immunized subcutaneously with a commercial 23-valent S. pneumonia polysaccharide vaccine (Pnu-Imune, 0.5 μg/serotype) and different doses of QS-21 in PBS, in 4 mg/ml Polysorbate 80 in PBS, or in 16 mg/ml hydroxypropyl-β-cyclodextrin in PBS. Anti-Type 14 IgG was determined by EIA on sera collected at day 7 after a single immunization. Neither Polysorbate 80 or hydroxypropyl-β-cyclodextrin in the formulation reduced the potency of the vaccine for stimulating an IgG3 response specific for Type 14 polysaccharide serotype.

Example 5

Clinical Studies of Compositions-Trial 1

Figure 3:
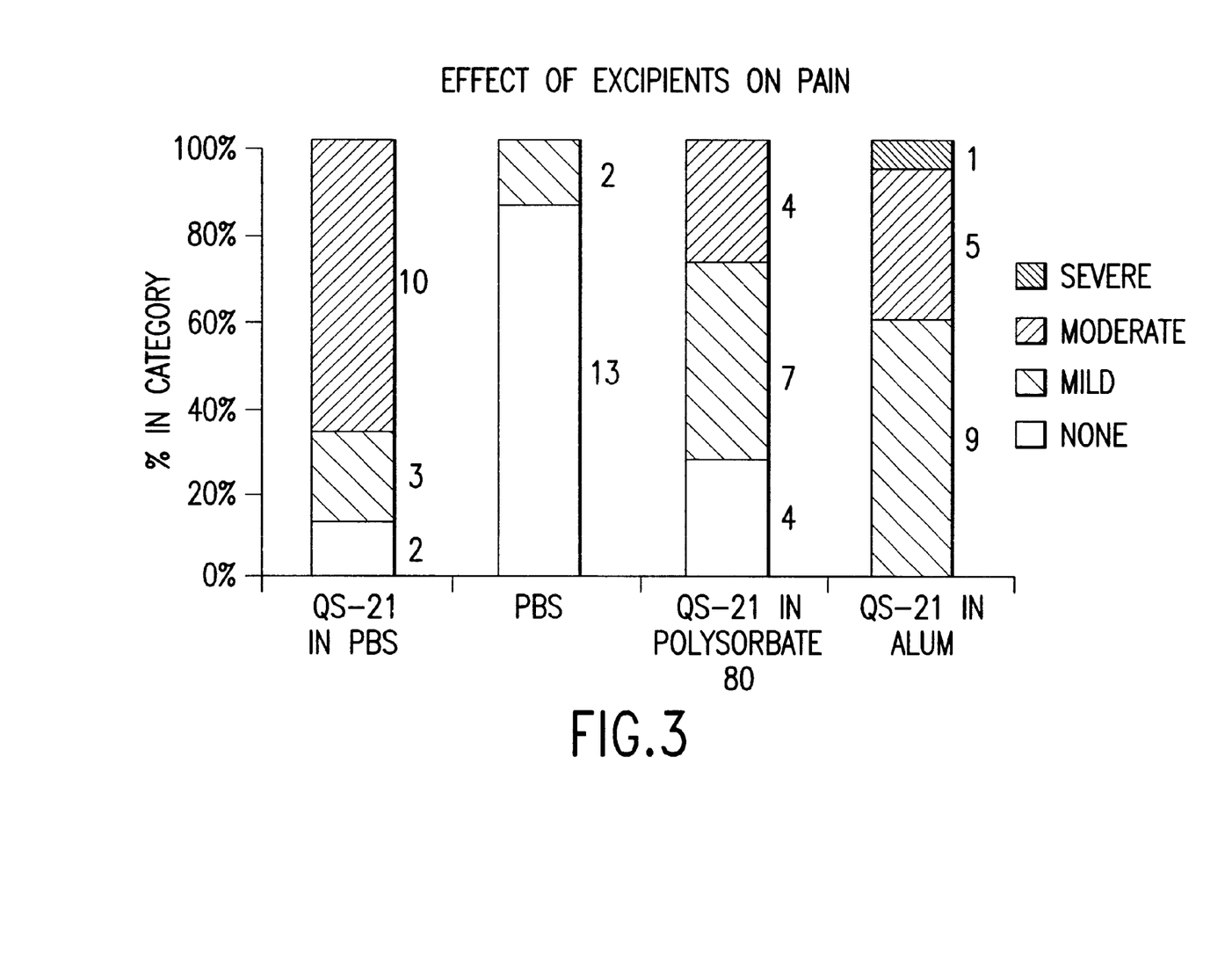
FIG. 3 shows a bar graph of patients' tolerance to pain for various excipients in QS-21 adjuvant compositions from Trial 1. This figure shows how the pain scores are classified as no pain, mild pain, moderate pain, or severe pain, where 0=no pain, 1–3=mild pain, 4–7=moderate pain, and 8–10= severe pain.
Figure 4:
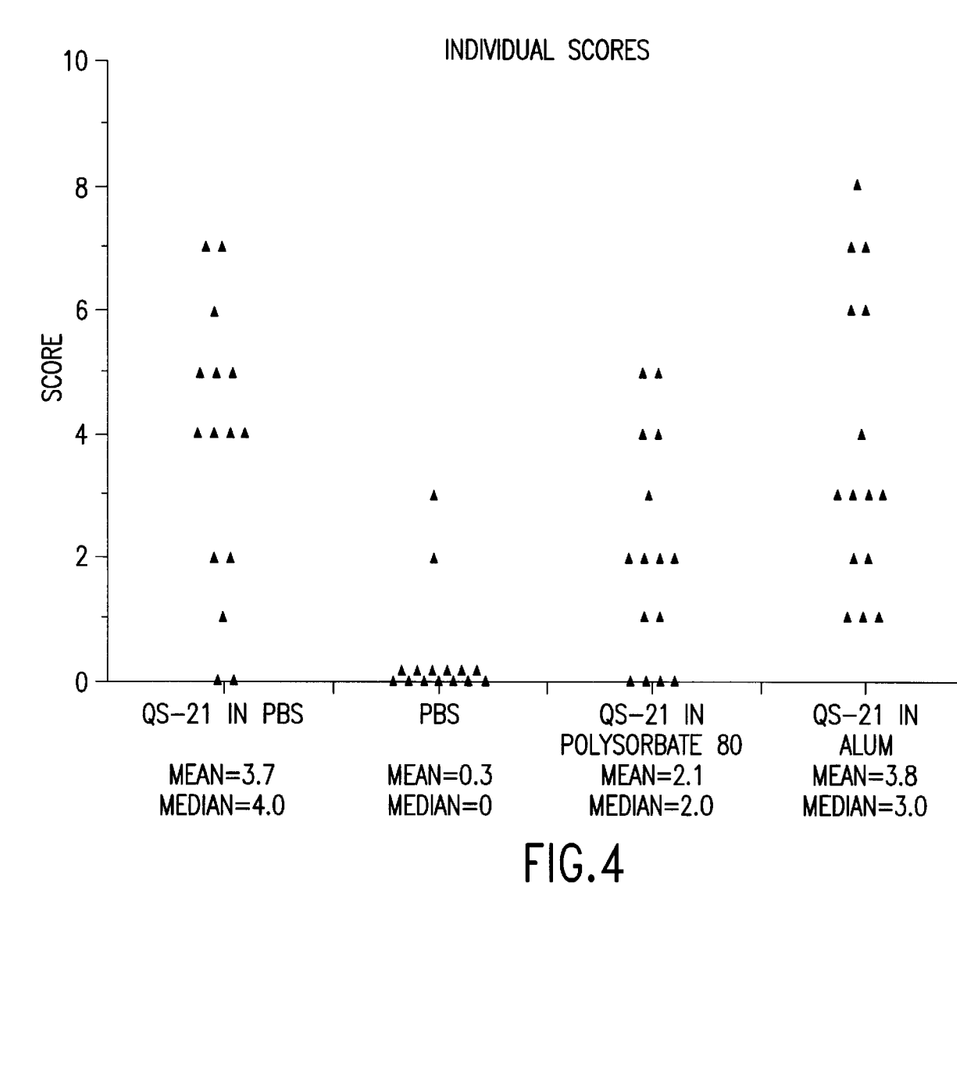
FIG. 4 shows the individual scores for the patients' tolerance to pain in FIG. 3. This figure shows individual immediate pain scores after injection of a given formulation on a scale of 0–10, where 0 is no pain and 10 is maximum pain.

Various QS-21 compositions were administered to patients in order to test for the compositions' pain tolerance. Fifteen volunteers were recruited to receive four intramuscular injections, with each injection given at one week intervals. The study was carried out as a randomized, double-blind study. Three of the formulations contained 50 μg QS-21 in either Dulbecco's PBS (without calcium or magnesium), in 4 mg/ml Polysorbate 80 in PBS, or in 1 mg/ml aluminum hydroxide in saline. The fourth formulation was a PBS control without QS-21. Volunteers were asked to rate the immediate pain in the first five minutes after injection on a 0 to 10 scale (0=no pain, 1–3=mild, 4–7=moderate, 8–10=severe). The results are shown in FIG. 3. The cumulative scores represented in FIG. 3 of the patients' tolerance to pain is represented in FIG. 4 as individual scores. The QS-21 formulation containing 4 mg/ml Polysorbate 80 resulted in an improved pain tolerance compared to QS-21 in PBS. The highest score for this particular formulation was rated as a 5.

Example 6

Clinical Studies of Compositions-Trial 2

Figure 5:
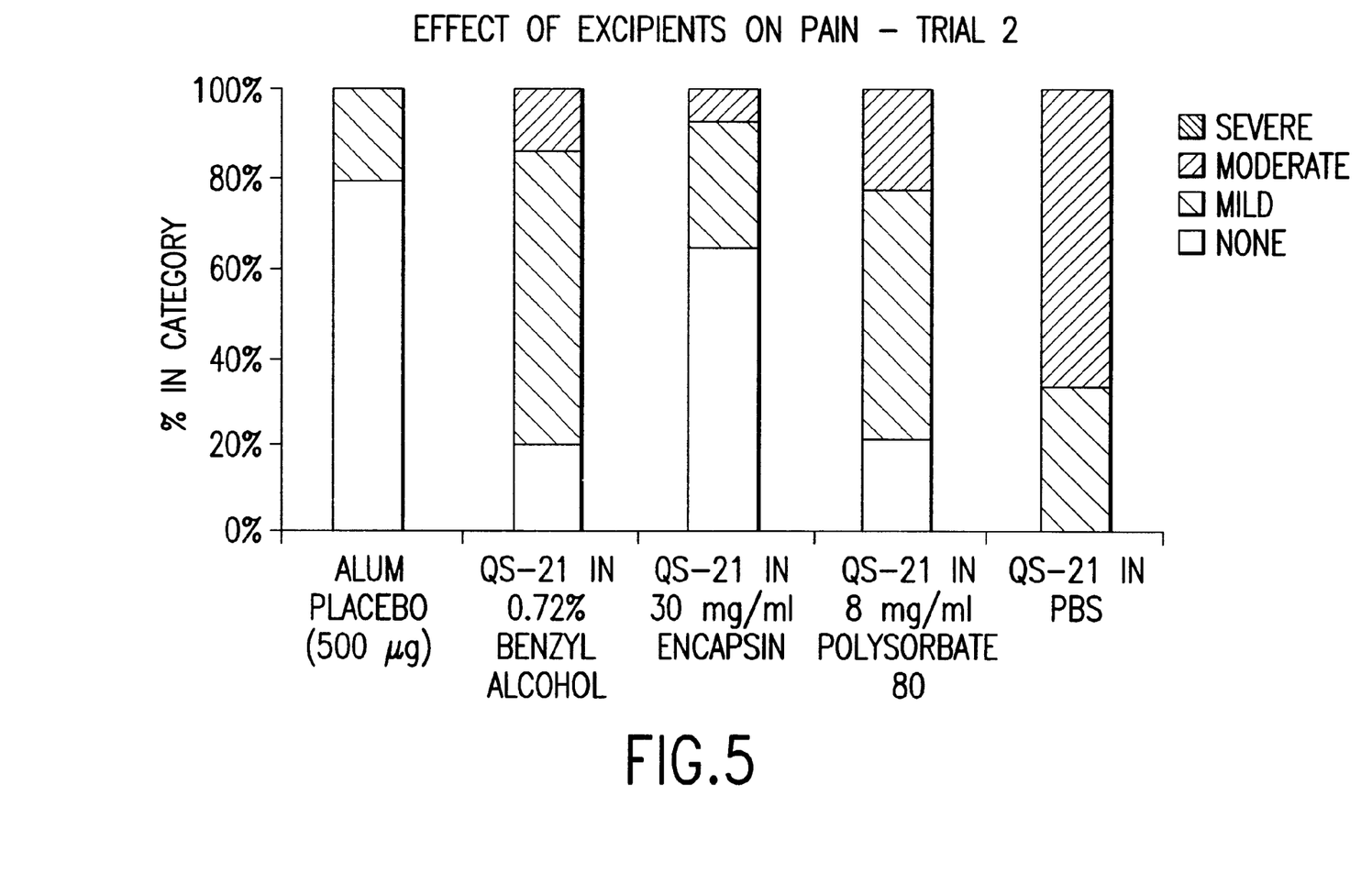
FIG. 5 shows a bar graph of patients' tolerance to pain for various excipients in QS-21 adjuvant compositions from Trial 2. This figure shows how the pain scores are classified as no pain, mild pain, moderate pain, or severe pain, where 0=no pain, 1–3=mild pain, 4–7=moderate pain, and 8–10= severe pain.
Figure 6:
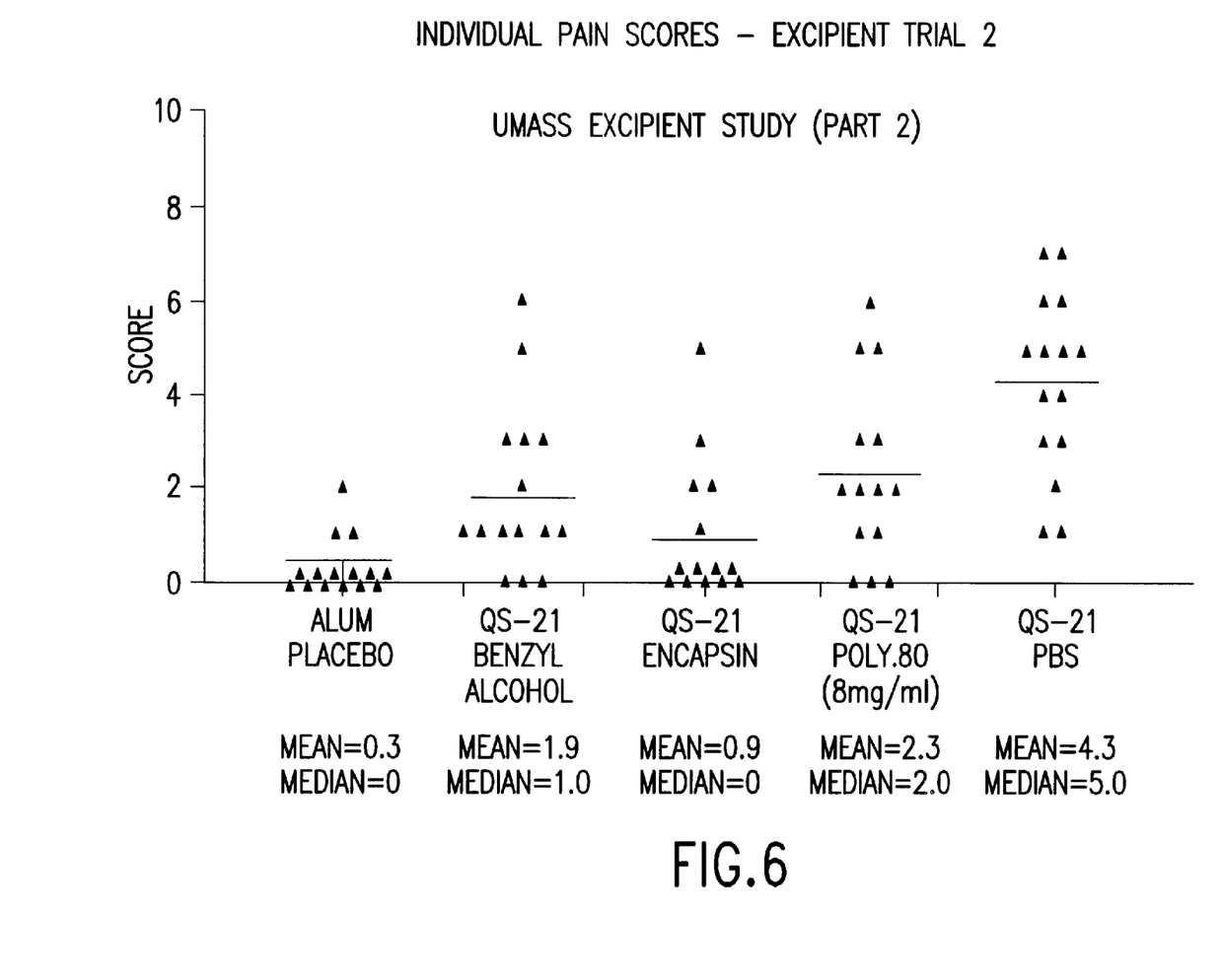
FIG. 6 shows the individual scores for the patients' tolerance to pain in FIG. 5. This figure shows individual immediate pain scores after injection of a given formulation on a scale of 0–10, where 0 is no pain and 10 is maximum pain. Mean and median scores for each formulation are listed below each formulation.

Various other QS-21 compositions were administered to patients in order to test for the compositions' pain tolerance. Fifteen volunteers were recruited to receive four intramuscular injections, with each injection given at one week intervals. The study was carried out as a randomized, double-blind study. The excipients evaluated were benzyl alcohol, hydroxypropyl-beta-cyclodextrin, and a higher dose of Polysorbate 80, which had been shown to be more effective than 4 mg/ml Polysorbate 80 at reducing QS-21 lysis of red blood cells in vitro. The five formulations tested were (1) 1 mg/ml aluminum hydroxide, which served as the placebo control; (2) 50 μg QS-21 in 0.72% benzyl alcohol in saline; (3) 50 μg QS-21 in 30 mg/ml hydroxypropyl-β-cyclodextrin; (Encapsin, Janssen Biotech N.V., Olen, Belgium) (4) 50 μg QS-21 in 8 mg/ml Polysorbate 80; and (5) 50 μg QS-21 in PBS (Dulbecco's PBS without calcium or magnesium), which served as a positive control formulation. Volunteers were asked to rate the immediate pain in the first five minutes after injection on a 0 to 10 scale (0=no pain, 1–3=mild, 4–7=moderate, 8–10=severe). The results are shown in FIG. 5. The cumulative scores represented in FIG. 5 of the patients' tolerance to pain is represented in FIG. 6 as individual scores. All excipients were shown to reduce the mean and median pain scores associated with QS-21 in PBS. The highest single score for the QS-21/Encapsin-formulation-was-rated as a 5, which compared more favorably with the QS-21/Polysorbate 80 formulation that was rated with a single 6 and two 5's.

The invention now being fully described, it will be apparent to one of ordinary skill in the art that many changes and modifications can be made thereto without departing from the spirit or scope of the invention as set forth below.

We claim:

1. A composition comprising an antigen or a nucleic acid encoding an antigenic peptide or protein, a saponin adjuvant, and an excipient selected from the group consisting of a β cyclodextrin and human serum albumin.

2. The composition according to claim 1, wherein the saponin adjuvant is a heterogenous saponin adjuvant.

3. The composition according to claim 2, wherein the heterogenous saponin adjuvant is Quil-A.

4. The composition according to claim 1, wherein the saponin adjuvant is a substantially pure saponin adjuvant.

5. The composition according to claim 4, wherein the substantially pure saponin adjuvant is QS-7 or QS-21.

6. The composition according to claim 1, wherein the antigen is a peptide, a protein, a polysaccharide, or a lipid.

7. The composition according to claim 1, wherein the excipient is a β cyclodextrin.

8. The composition according to claim 7, wherein the β cyclodextrin is hydroxypropyl β cyclodextrin.

9. The composition according to claim 1, wherein the excipient is human serum albumin.

10. A composition comprising an antigen or a nucleic acid encoding an antigenic peptide or protein, a saponin adjuvant and an excipient, wherein the excipient is DS-1.

11. The composition according to claim 10, wherein the saponin adjuvant is a heterogenous saponin adjuvant.

12. The composition according to claim 11, wherein the heterogenous saponin adjuvant is Quil-A.

13. The composition according to claim 10, wherein the saponin adjuvant is a substantially pure saponin adjuvant.

14. The composition according to claim 13, wherein the substantialy pure saponin adjuvant is QS-7 or QS-21.

15. The composition according to claim 10, wherein the antigen is a peptide, a protein, a polysaccharide, or a lipid.

* * * * *